US012578407B2

(12) United States Patent
Guo

(10) Patent No.: US 12,578,407 B2
(45) Date of Patent: Mar. 17, 2026

(54) ULTRA-FAST ARTERIAL SPIN LABELING WITH NARROW-BAND VELOCITY-SELECTIVE (NB-VS) LABELING

(71) Applicant: The Regents of the University of California, Oakland, CA (US)

(72) Inventor: Jia Guo, Yorba Linda, CA (US)

(73) Assignee: The Regents of the University of California, Oakland, CA (US)

(*) Notice: Subject to any disclaimer, the term of this patent is extended or adjusted under 35 U.S.C. 154(b) by 263 days.

(21) Appl. No.: 18/554,758

(22) PCT Filed: Apr. 1, 2022

(86) PCT No.: PCT/US2022/023126
§ 371 (c)(1),
(2) Date: Oct. 10, 2023

(87) PCT Pub. No.: WO2022/221076
PCT Pub. Date: Oct. 20, 2022

(65) Prior Publication Data
US 2025/0004083 A1      Jan. 2, 2025

Related U.S. Application Data

(60) Provisional application No. 63/175,448, filed on Apr. 15, 2021.

(51) Int. Cl.
*G01R 33/561* (2006.01)
*G01N 24/08* (2006.01)
(Continued)

(52) U.S. Cl.
CPC ........... *G01R 33/561* (2013.01); *G01N 24/08* (2013.01); *G01N 33/4833* (2013.01); *G01R 33/56366* (2013.01)

(58) Field of Classification Search
CPC ...... G01R 33/561; A61B 5/055; G01N 24/08; G01N 33/4833; G01N 33/5607
(Continued)

(56) References Cited

U.S. PATENT DOCUMENTS

| | | | |
|---|---|---|---|
| 2,473,318 A | 6/1949 | Donald | |
| 4,988,947 A | 1/1991 | Ugurbil et al. | |

(Continued)

FOREIGN PATENT DOCUMENTS

| | | | |
|---|---|---|---|
| CN | 109752683 A | 5/2019 | |
| CN | 110197106 A | 9/2019 | |

(Continued)

OTHER PUBLICATIONS

International Search Report and Written Opinion from PCT Application PCT/US2023/061384 dated Jun. 21, 2023.
(Continued)

*Primary Examiner* — Roberto Velez
(74) *Attorney, Agent, or Firm* — Perkins Coie LLP

(57) ABSTRACT

Techniques, systems and apparatus are described for magnetic resonance imaging. A method includes applying a radio frequency (RF) signal of a predetermined time duration towards a target, wherein the RF signal comprises a composite pulse that includes a velocity-selective pulse comprising RF pulses whose phase shift is modulated over the predetermined time duration, acquiring a magnetic resonance signal from the target resulting from the application of the RF signal, and generating an MRI image of the target from the magnetic resonance signal.

20 Claims, 9 Drawing Sheets

(51) Int. Cl.
G01N 33/483 (2006.01)
G01R 33/563 (2006.01)

(58) Field of Classification Search
USPC ................................................ 324/308, 309
See application file for complete search history.

(56) References Cited

U.S. PATENT DOCUMENTS

| | | | | |
|---|---|---|---|---|
| 7,587,233 | B2 | 9/2009 | Wong et al. | |
| 8,212,560 | B2 * | 7/2012 | Moeller | G01R 33/4824 |
| | | | | 324/309 |
| 12,282,080 | B1 | 4/2025 | Guo | |
| 2005/0277825 | A1 * | 12/2005 | Wong | G01R 33/56341 |
| | | | | 600/410 |
| 2008/0281186 | A1 * | 11/2008 | Kuhara | G01R 33/5635 |
| | | | | 600/413 |
| 2010/0030062 | A1 | 2/2010 | Bolar et al. | |
| 2010/0191099 | A1 | 7/2010 | Salerno et al. | |
| 2012/0268126 | A1 | 10/2012 | Guo et al. | |
| 2012/0283547 | A1 | 11/2012 | Wong et al. | |
| 2015/0309134 | A1 | 10/2015 | Meakin et al. | |
| 2015/0323630 | A1 | 11/2015 | Weingartner et al. | |
| 2017/0160365 | A1 * | 6/2017 | Helle | G01R 33/56366 |
| 2017/0176564 | A1 * | 6/2017 | Qin | G01R 33/56563 |
| 2017/0293008 | A1 * | 10/2017 | Qin | G01R 33/50 |
| 2019/0310337 | A1 | 10/2019 | Carinci et al. | |
| 2020/0284864 | A1 | 9/2020 | Damen et al. | |
| 2023/0329576 | A1 | 10/2023 | Bonanno et al. | |
| 2025/0060441 | A1 | 2/2025 | Guo | |
| 2025/0116739 | A1 | 4/2025 | Guo et al. | |

FOREIGN PATENT DOCUMENTS

| | | | |
|---|---|---|---|
| WO | 2015158879 | A1 | 10/2015 |
| WO | 2022221076 | A1 | 10/2022 |
| WO | 2023150468 | A1 | 8/2023 |

OTHER PUBLICATIONS

International Search Report and Written Opinion mailed Jun. 16, 2022 for International Patent Application No. PCT/US2022/023126 (17 pages).

Guo, Jia , et al., "An optimized design to reduce eddy current sensitivity in velocity-selective arterial spin labeling using symmetric BIR-8 pulses", Magnetic Resonance in Medicine, 73(3)., 2015, 1085-1094.

Guo, Jia , et al., "Comparison of velocity-selective arterial spin labeling schemes", Magnetic Resonance in Medicine; 85(4)., 2021, 2027-2039.

Guo, Jia, et al., "Increased SNR Efficiency in Velocity Selective Arterial Spin Labeling Using Multiple Velocity Selective Saturation Modules (mm-VSASL)", Magnetic Resonance in Medicine; 74., 2015, 694-705.

Guo, Jia , "Robust dual-module velocity-selective arterial spin labeling (dm-VSASL) with velocity-selective saturation and inversion", Magnetic Resonance in Medicine; 89(3)., 2023, 1026-1040.

Qin, Qin , et al., "Velocity-Selective-Inversion Prepared Arterial Spin Labeling", Magnetic Resonance in Medicine; 76., 2016, 1136-1148.

Wong, Erin C., et al., "Velocity-selective arterial spin labeling", Magnetic Resonance in Medicine; 55(6)., Jun. 2006, 1334-41.

Ye, Frank Q., et al., "Noise reduction in 3D perfusion imaging by attenuating the static signal in arterial spin tagging (ASSIST)", Magnetic Resonance in Medicine; 44(1)., 2000, 92-100.

Buxton et al. "A General Kinetic Model for Quantitative Perfusion Imaging with Arterial Spin Labeling," Magnetic Resonance in Medicine, Sep. 1998, 40(3):383-396.

Liu et al. "A mathematical model for velocity-selective arterial spin labeling," Magnetic Resonance in Medicine, Apr. 2024, 91(4):1384-1403.

Woods et al. "Recommendations for quantitative cerebral perfusion MRI using multi-timepoint arterial spin labeling: Acquisition, quantification, and clinical applications," Magnetic Resonance in Medicine, Aug. 2024, 92(2):469-495.

* cited by examiner

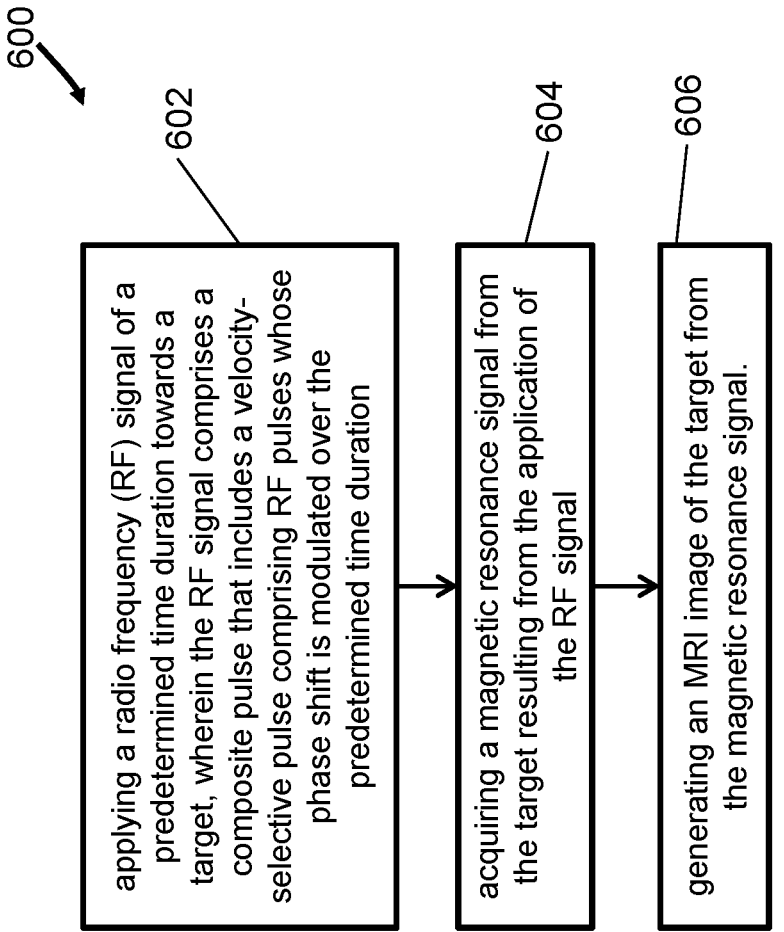

600

602 applying a radio frequency (RF) signal of a predetermined time duration towards a target, wherein the RF signal comprises a composite pulse that includes a velocity-selective pulse comprising RF pulses whose phase shift is modulated over the predetermined time duration

604 acquiring a magnetic resonance signal from the target resulting from the application of the RF signal

606 generating an MRI image of the target from the magnetic resonance signal.

FIG. 6

ULTRA-FAST ARTERIAL SPIN LABELING WITH NARROW-BAND VELOCITY-SELECTIVE (NB-VS) LABELING

PRIORITY CLAIM

This patent document is a 371 National Stage Application of International Patent Application No. PCT/US2022/023126, filed Apr. 1, 2022, which claims the benefit of priority of U.S. Provisional Application 63/175,448, filed on Apr. 15, 2021, which are incorporated by reference as part of the disclosure of this document.

TECHNICAL FIELD

This patent document relates to systems, devices, and processes for magnetic resonance imaging.

BACKGROUND

Imaging through Magnetic Resonance Imaging (MRI) techniques has been widely applied in imaging applications in medical, biological and other fields. A typical MRI technique produces an image of a selected body part of an object under examination by manipulating the magnetic spins in a body part and processing measured responses from the magnetic spins. An MRI system may include hardware to generate different magnetic fields for imaging, including a static magnetic field along a Z-direction to polarize the magnetic spins, gradient fields along mutually orthogonal X, Y, or Z directions to spatially select a body part for imaging, and a radio frequency (RF) magnetic field to manipulate the spins.

SUMMARY

Techniques, systems and apparatus are described for a magnetic resonance imaging (MRI) system for modifying the shape/thickness of the excitation/inversion slab to improve the temporal signal-to-noise ratio (tSNR) of arterial spin labeling (ASL) imaging.

In one example aspect, a disclosed method includes applying a radio frequency (RF) signal of a predetermined time duration towards a target, wherein the RF signal comprises a composite pulse that includes a velocity-selective pulse comprising RF pulses whose phase shift is modulated over the predetermined time duration, acquiring a magnetic resonance signal from the target resulting from the application of the RF signal: and generating an MRI image of the target from the magnetic resonance signal.

In another example aspect, a disclosed apparatus comprises a scanner comprising a magnet, gradient coils and a radio frequency (RF) and a data processing system in communication with the scanner to receive acquired magnetic resonance signals and generate an MRI image of the target from the magnetic resonance signal.

Those and other aspects and associated implementations and benefits of the disclosed technology are described in greater detail in the drawings, the description and the claims.

BRIEF DESCRIPTION OF THE DRAWINGS

FIG. 6 is a flowchart of an example method of operating an MRI system.

DETAILED DESCRIPTION

In recent years, advances in magnetic resonance imaging (MRI) technology have led to emergence of MRI imaging systems that provide better image clarity for medical diagnostic purpose than previous MRI systems. However, certain medical applications still present a challenge to present day MRI systems. For example, in complex body parts where many blood capillaries carry blood, fast and accurate imaging using MRI is still a difficult procedure. In particular, MRI imaging for detection of brain tumors pose a challenging problem due to blood flow in a large number of blood vessels and at the same time a need to minimize the amount of time for which a brain is exposed to MRI radiation. Clinically satisfactory performance of typical conventional techniques is limited to situations where blood flow is slow. Furthermore, the repetition time (TR) of conventional technique could be as high as 2.5 to 3 seconds, which may be unacceptable in certain situations.

The techniques described in the present document may be used by embodiments of MRI systems for achieving temporal and/or spatial resolution of MRI imaging that is far superior than conventional MRI techniques.

As further described in the present document, in some embodiments, a narrow-band velocity selectivity can be realized using the disclosed techniques. For example, Fourier transform based velocity-selective inversion (FT-VSI) waveforms as described herein may be used to achieve such results.

In some disclosed embodiments, a novel strategy to improve the temporal resolution and/or signal to noise ratio (SNR) efficiency of perfusion imaging using velocity-selective (VS) labeling may be achieved by labeling spins within a narrow velocity band. This strategy allows faster recovery/refreshment of the magnetization of arterial spins for improved SNR efficiency and temporal resolution. A few implementation methods of such labeling strategy were explored, using modified Fourier-transform based VS pulses, including VSI pulses. The SNR efficiency and achievable temporal resolution were examined by ASL signal modeling, demonstrating a good promise for ultra-fast perfusion imaging with high SNR efficiency.

1. Introduction

Figures 1A, 1B:
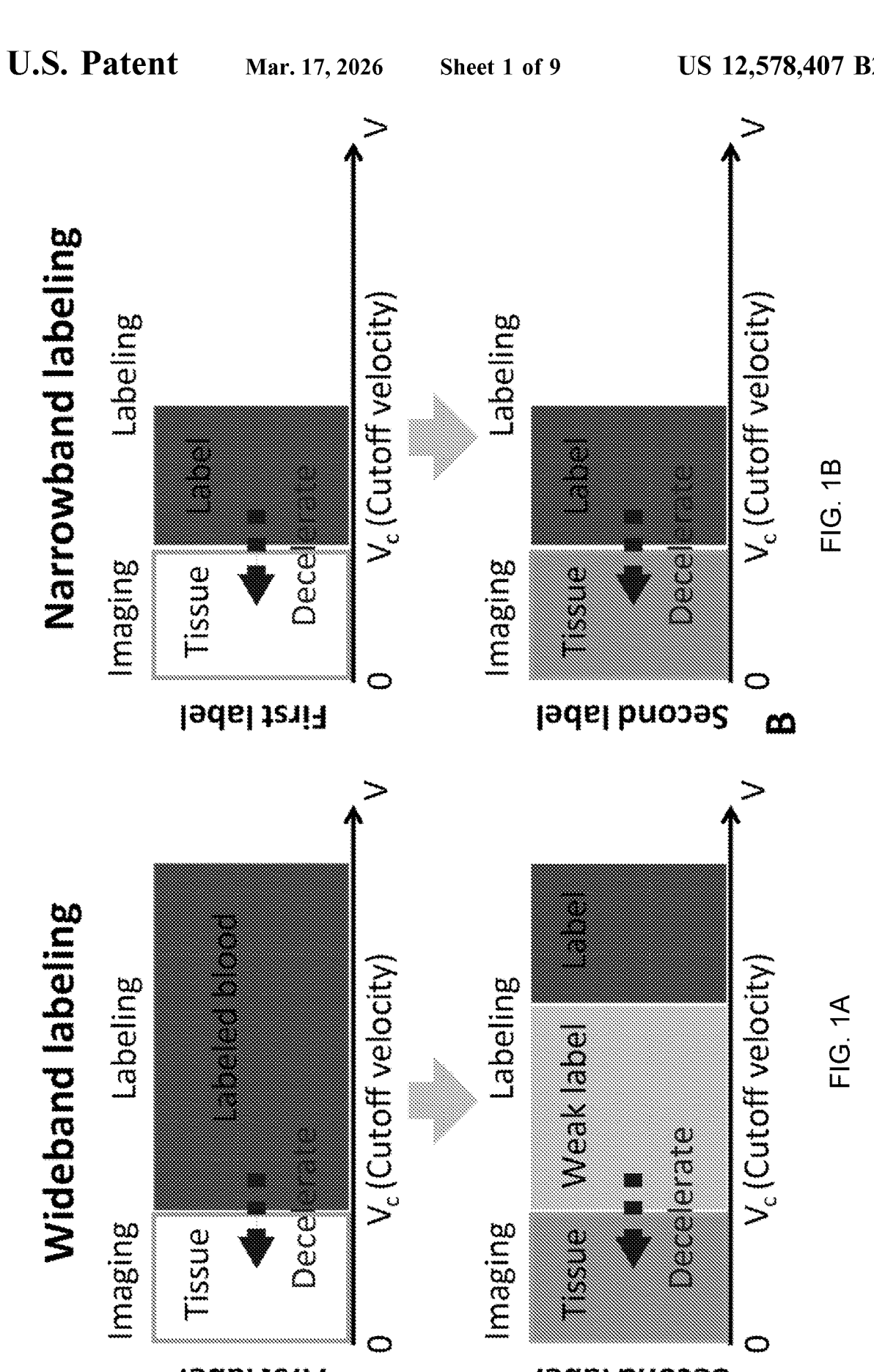
FIGS. 1A-1B show examples of schematics showing that narrow-band velocity selectivity allows ultra-fast perfusion imaging with high SNR efficiency, while conventional VSASL (wide-band labeling) may suffer from reduced SNR efficiency due to multiple labeling on the same bolus.

Velocity-selective arterial spin labeling (VSASL) is insensitive to inhomogeneous transit times. This feature permits a short post-label delay (PLD), suitable for fast perfusion imaging to study brain functions. Conventional VSASL methods label globally and target a wide band of velocities for a large bolus duration (BD) for a strong perfusion signal. When imaging with a short TR for high temporal resolution, multiple labeling pulses may be applied on the same bolus, resulting in reduced perfusion signal due to multiple saturation/inversion, as shown in FIG. 1A. As shown in FIG. 1A, a first label is applied showing the effect along the velocity axis (horizontal axis) in which tissue being imaged is depicted up to a cutoff velocity Vc and labeled blood at higher velocities. At the time of application of the second pulse, the effect of the second pulse results in a weaker label, resulting in lower signal to noise ratio SNR in captured response. Further details are discussed in Sections 5 and 6 of the present document.

In some implementations, slice selectivity may be incorporated into VSASL to limit the BD for fast perfusion imaging. However, the slice coverage may be limited with potential dependence on the vasculature orientation, and the labeling efficiency may be suboptimal due to saturation-based labeling. The techniques described herein may be used by embodiments to limit the BD by inverting spins with narrow-band velocity-selectivity (nb-VS), aiming for ultrafast perfusion imaging with improved SNR, while keeping the labeling geometry-independent for a good coverage. Theoretical SNR efficiency of three major categories of ASL methods were also compared in the context of fast perfusion imaging.

2. Example Embodiments

As demonstrated in FIG. 1B, labeling spins within a relatively narrow band of velocities allows detection of the proximal label while keeping the spins at higher velocities unperturbed as fully relaxed probe for the next measurement. Here, it is shown that the first label is relatively narrower band along the velocity axis, compared to the conventional technique of FIG. 1A. For example, in FIG. 1A, the cutoff velocity may be a predetermined threshold such as approximately 2 cm/sec while the labeled blood velocity may extend to 40 cm/sec. By comparison, in FIG. 1B, the labeling may extend only up to around 8 to 10 cm/sec, preferably less than 20 cm/sec, which is much narrower than FIG. 1A. Further, as shown in FIG. 1B, the application of the second label does not suffer from degradation in SNR due to multiple labeling of the same bolus as depicted in FIG. 1A.

Figure 2A:
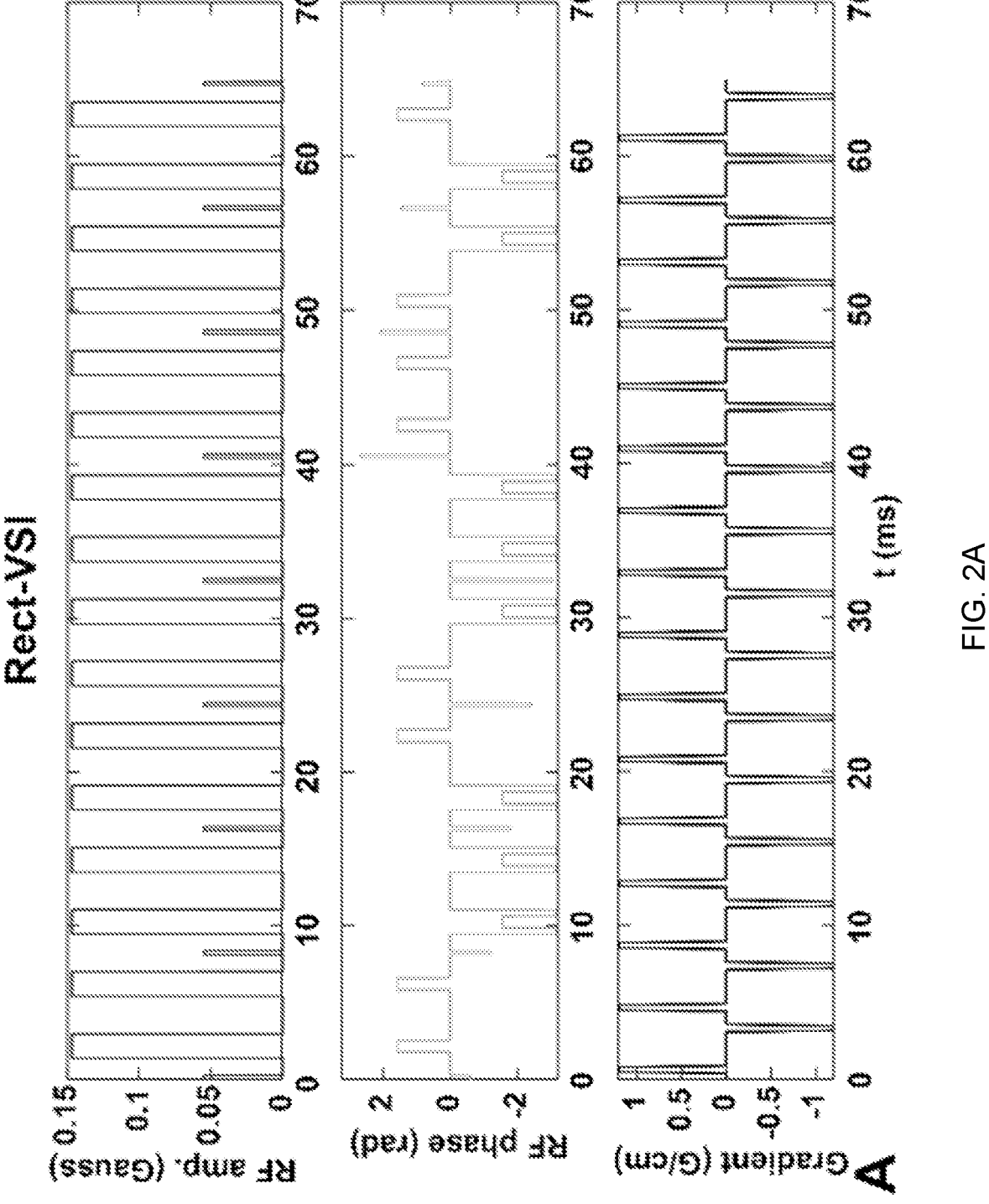
FIGS. 2A-2B show examples of the proposed pulses for narrow-band velocity-selective labeling, modified based on rect-VSI (velocity selective inversion) (FIG. 2A) and sinc-VSI (FIG. 2B) pulses.
Figure 2B:
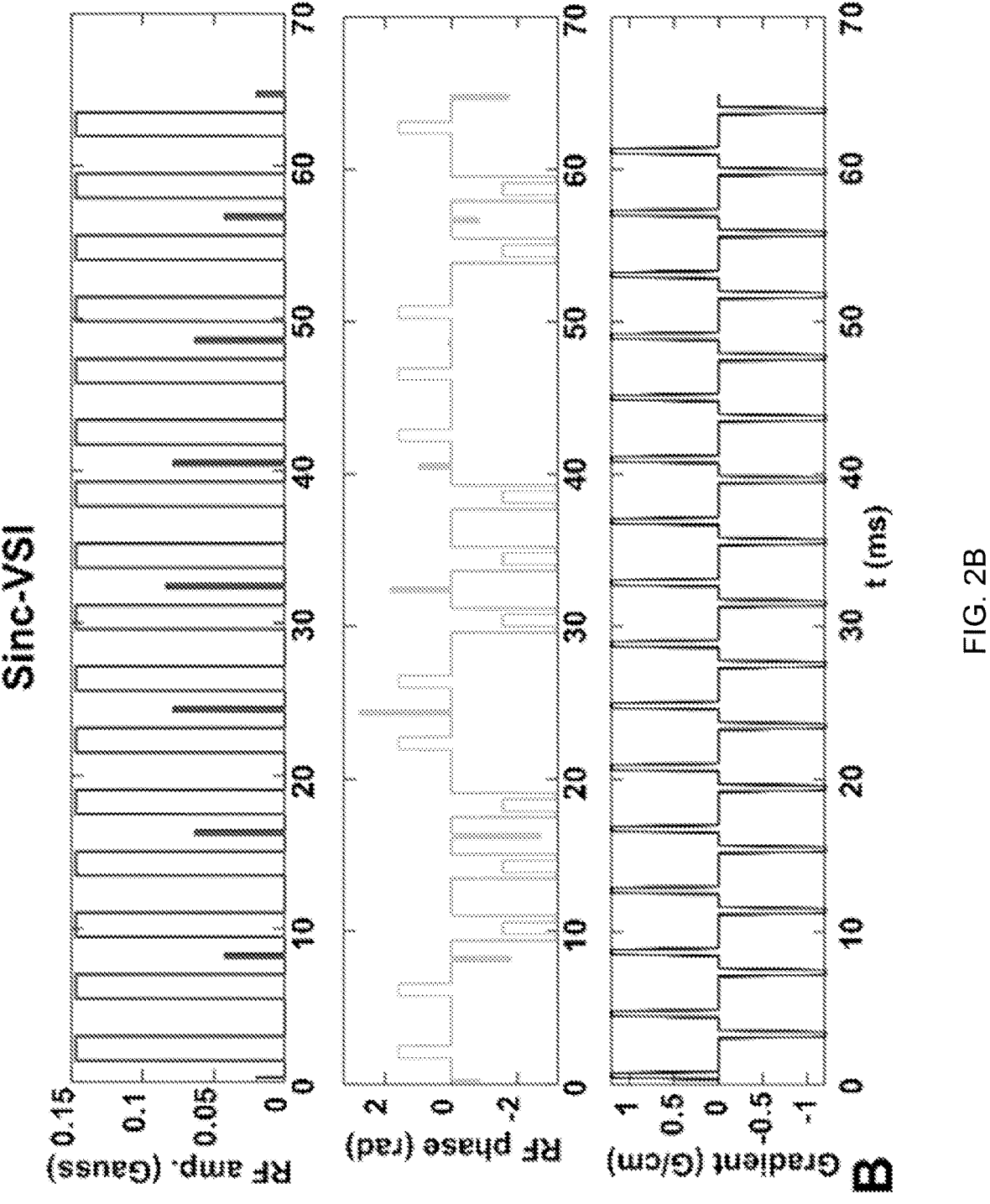

To implement nb-VS labeling, a sinc-modulated Fourier-transform based velocity-selective inversion (FT-VSI) pulse (sinc-VSI) was modified with: 1) linearly increasing phase shift on the RF pulses to shift the VS profile, so that spins moving at low velocities were inverted while the static and fast moving spins were unaffected: 2) the control condition was implemented without VS gradients. In general, the phase shift of the RF pulses may be modulated using one of several suitable functions, with the linearly increasing phase shift being one example of such functions. Other functions may include piece-wise linear or harmonic increments in phase shift. The nb-VS labeling using the original FT-VSI pulse (rect-VSI) was also constructed for comparison. Other modification may be as follows. In some embodiments, composite refocusing pulses with Malcom Levitt (MLEV-8) phase cycling patterns may be added. Such a modification may result in an improved $B_1$ insensitivity. In some embodiments, gaps may be added before and after gradient pulses to reduce eddy current sensitivity. The details of the pulses are shown in FIGS. 2A-2B. In FIG. 2A, a rectangular VSI pulse is depicted along the time dimension (horizontal axis), with top graph showing amplitude of the applied RF signal, the middle graph showing phase of the RF signal and the bottom graph showing gradient of the applied RF signal in Gauss per centimeter (cm) units. Corresponding graphs for a sinc-VSI pulse are shown in FIG. 2B.

To validate the performance of the proposed techniques, a Bloch simulation was performed in MATLAB2020b (The Mathworks, Nantick, MA) to study the nb-VS profiles in the presence of $B_1$ (0.7 to 1.3 of the nominal value, step size 0.1) and $B_0$ (−150 to 150 Hz, step size 50 Hz) variations, with arterial $T_1$ (1650 ms) and $T_2$ (150 ms) relaxation included. Additional details of Bloch simulations are provided in Section 7 of the present document.

To examine the SNR benefit of nb-VS quantitatively, the SNR efficiency ($Sig_{ASL}/\sqrt{acquisitiontime}$) was calculated by a kinetic arterial spin labeling (ASL) signal model[11] in the context of fast imaging (TR from 0.3 s to 3 s). Different labeling methods were compared, including: conventional saturation- and inversion-based VSASL (VSS and VSI, respectively, BD=2 s) where the magnetization was assumed to start from saturation: nb-VS labeling (BD=1 s) with fully relaxed magnetization: pulsed ASL (PASL, PLD=1 s, BD=1.2 s, labeling efficiency ($\alpha$)=0.98) with and pseudo-continuous ASL (PCASL, PLD=1.5 s, BD=∞, $\alpha$=0.85) with fully relaxed magnetization. $T_1$ and $T_2$ relaxation and an imaging time of 0.3 s were assumed. This method can be used for imaging with longer TR, e.g., TR>3 s.

3. Discussion of Results

Figure 3A:
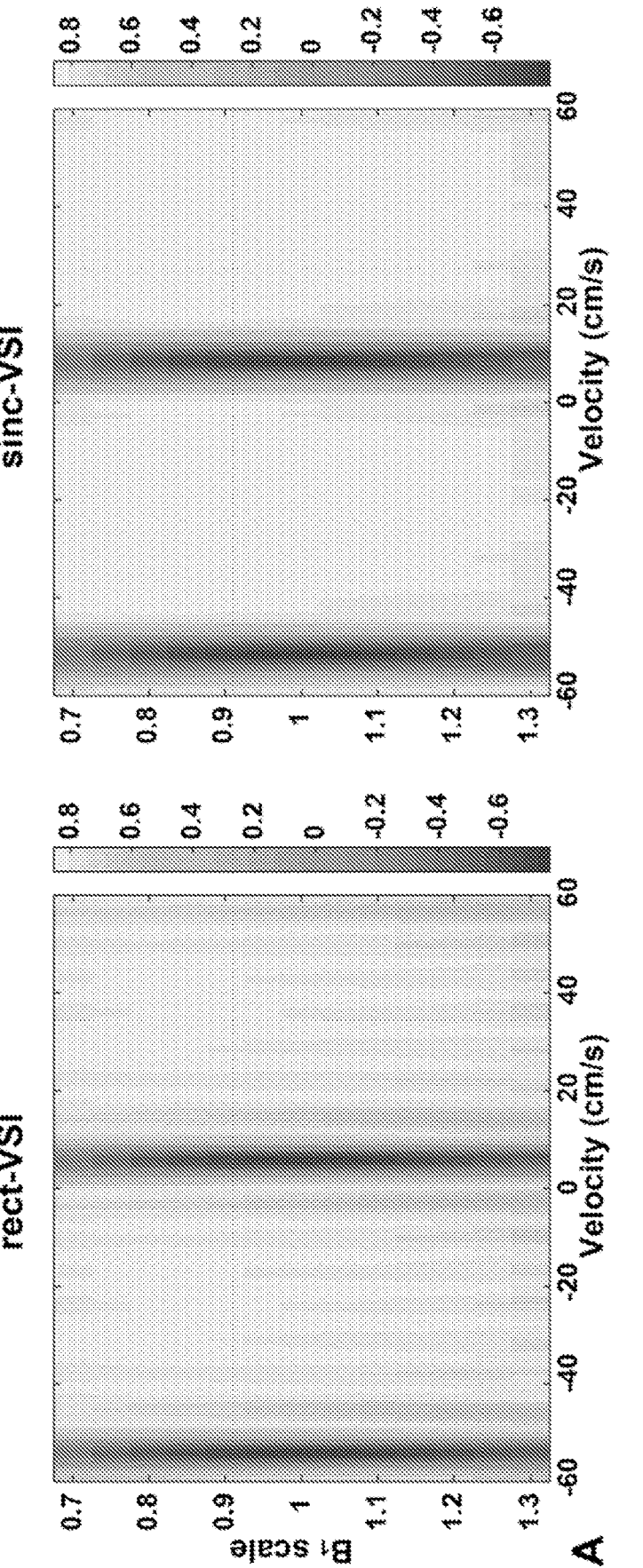
FIGS. 3A-3B show examples of velocity-selective profiles under the label condition for both modified rect-VSI and sinc-VSI labeling. Under the control condition, the magnetization response was the same across all velocities (not shown), of the same value at V=0 under the label condition.
Figure 3B:
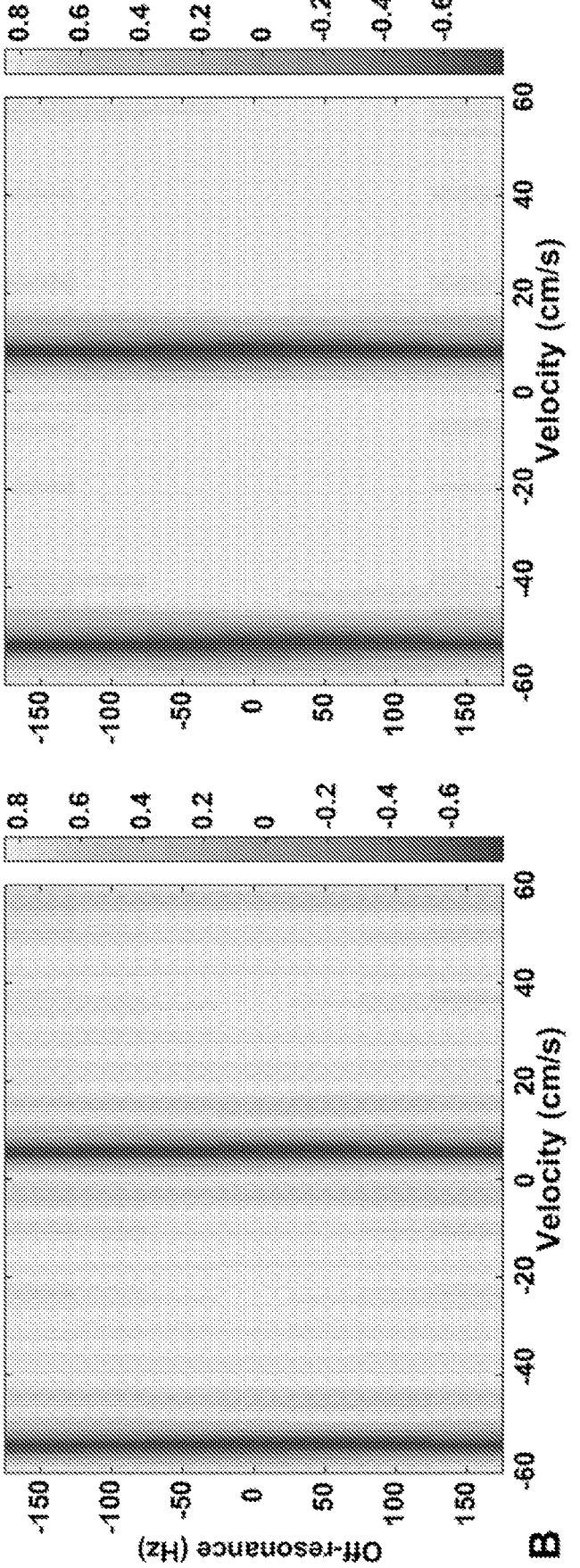

The nb-VS profiles are shown in FIG. 3A and FIG. 3B. FIG. 3A shows a plot of velocity along horizontal axis and $B_1$ scale vertical axis for rect-VSI (left) and sinc-VSI (right). FIG. 3B shows Off-resonance (vertical axis) as a function of velocity for rect-VSI (left) and sinc-VSI (right). Under the control conditions, the magnetization response was the same across all velocities of the same value of V=0 under the label condition.

Figures 4A, 4B:
FIGS. 4A-4B show examples of velocity-selective profiles under the label condition using the sinc-modulated FT-VS saturation for nb-VS labeling.

Both rect-VSI and sinc-VSI based pulses were capable of labeling spins in a narrow velocity band with reasonable robustness against field inhomogeneities. The sinc-VSI pulse produced much smoother response in the "unperturbed" velocity bands and slightly wider inversion bands compared to rect-VSI. FT-VSS-based nb-VS labeling (nb-VSS) was also feasible, albeit with a higher $B_1$ sensitivity (FIGS. 4A-4B).

Figure 5:
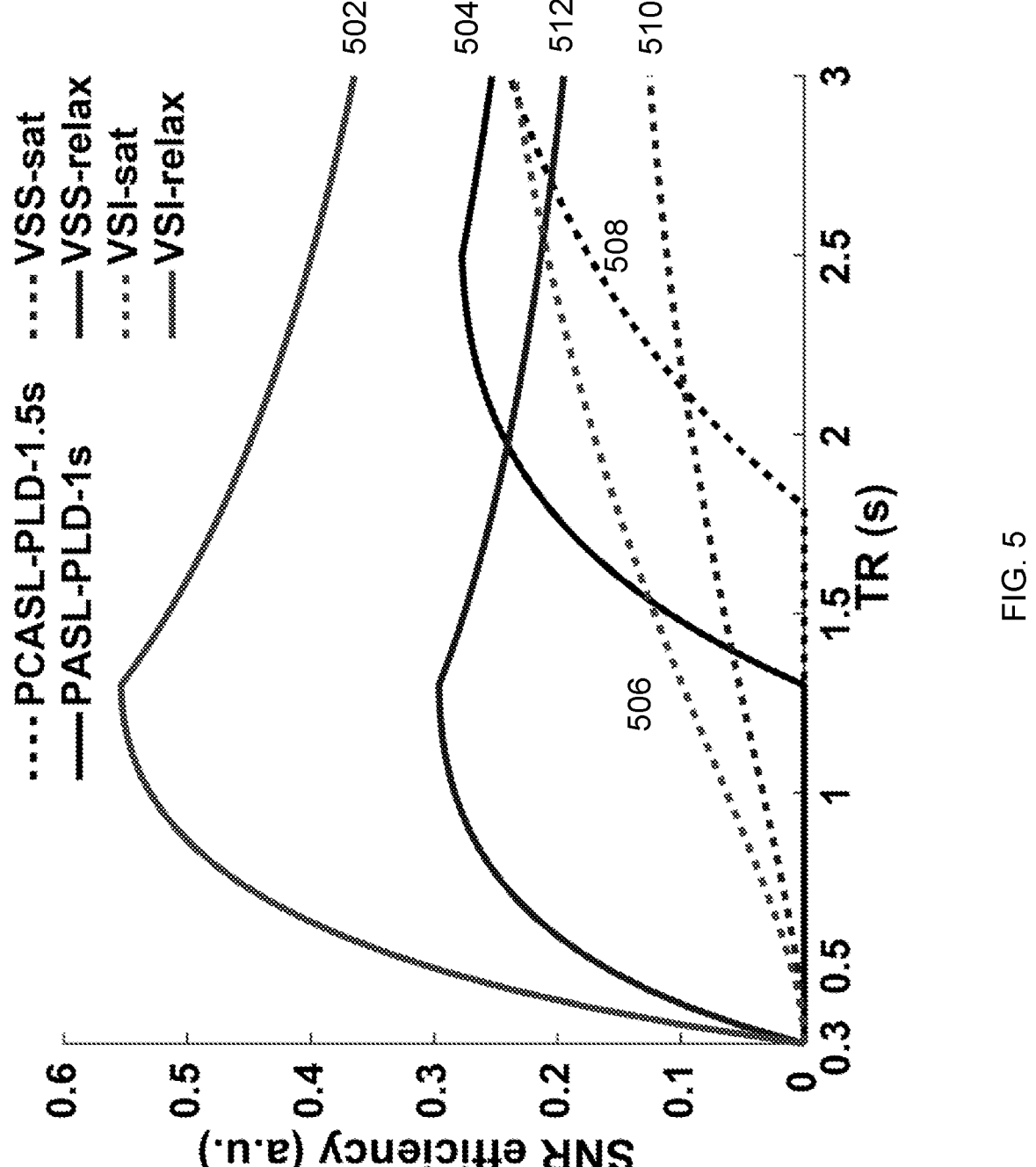
FIG. 5 shows an example of comparison of SNR efficiencies of different labeling methods.

The SNR efficiencies of different labeling methods are shown in FIG. 5. In this graph, curve 502 corresponds to velocity selective inversion labeling method assuming relaxed magnetization (VSI-relax, using nb-VSI), curve 504 corresponds to pulsed-ASL labeling method assuming a post-labeling delay (PLD) of 1 second (PASL-PLD-1second), curve 506 corresponds to velocity selective inversion labeling method assuming saturated magnetization (VSI-sat, using wide-band VSI), curve 508 corresponds to pseudo-continuous ASL labeling method assuming a PLD of 1.5 second (PCASL-PLD-1.5second), curve 510 corresponds to velocity selective saturation (VSS) labeling method assuming saturated magnetization (VSS-sat, using wide-band VSS) and curve 512 corresponds to velocity selective saturation labeling method assuming relaxed magnetization (VSS-relax, using nb-VSS).

With nb-VS labeling, full relaxation significantly boosted the SNR efficiencies at very short TRs. The inversion-based labeling had the highest SNR efficiency, twice of that with the saturation-based labeling. Conventional VS labeling had much lower SNR efficiency due to the need for the magnetization to recover. For PASL and PCASL, the temporal resolution was limited by the PLD and the SNR efficiencies were lower than nb-VS labeling. For PASL, the optimal TR of around 2.5 s matched with the values typically used in PASL-based fMRI.

As can be seen from FIG. 5, VSS-sat (510) and VSI-sat (506), which represent conventional VSASL with wide-band velocity selectivity, where the arterial magnetization is assumed to recover from saturation show lower SNR for same TR compared to VSS-relax (512) and VSI-relax (502) were nb-VS labeling where the arterial magnetization was assumed to be fully relaxed. Similarly, PASL (504) and PCASL (508) also show inferior performance to curves 501 and 512. Note different BDs for different methods: 2 s for VSS-sat and VSI-sat: 1 s for VSS-relax and VSI-relax, 1.2 s for PASL: and unlimited for PCASL.

FIG. 6 shows an example method 600 method of operating a magnetic resonance imaging (MRI) system. The method 600 includes applying (602) a radio frequency (RF) signal of a predetermined time duration towards a target. The RF signal comprises a composite pulse that includes a velocity-selective pulse comprising RF pulses whose phase shift is modulated over the predetermined time duration. Some examples of the composite pulse are discussed with reference to FIGS. 3A-3B. In some embodiments, the modulation may comprise a predefined function, such as a linear function that increases over the time duration in a linear manner. In some embodiments, the predefined function may be a quadratic function of time. In some embodiments, an exponential function may be used. In some embodiments, the velocity-selective pulse may be a velocity-selective inversion pulse. In some embodiments, the time duration may be of the order of 10's of milliseconds, e.g., 10 to 100 milliseconds, or higher. The exact time duration may be configured according to the type of target or safety requirements for exposure of the target to magnetic radiation.

The method 600 includes acquiring (604) a magnetic resonance signal from the target resulting from the application of the RF signal. For example, the target may comprise a body part such as a brain and the acquisition may be performed within a TR time period (e.g., 1 second).

The method 600 includes, generating (606) an MRI image of the target from the magnetic resonance signal. The MRI image generation may be performed using a processor that executes a code. For example, the MRI image may be generated by processing the acquired magnetic resonance signal in a digital format, filtering to reduce noise, and processing for display on a user interface.

In some embodiments, the method 600 may include applying is performed by controlling spins generated in the target such that spins moving within a predetermined velocity band are magnetization-modulated while static and spins moving at velocities outside of the predetermined velocity band remain unaffected. For example, in some embodiments, the predetermined velocity band may be 0.5 cm/s to 20 cm/s. In some embodiments, a predetermined function may be used to modulate the phase shift. For example, a linear function may be used in some embodiments.

In some embodiments, the RF signal is applied with an intensity that does not create velocity-selectivity in the target. In some embodiments, to ensure that no velocity-selectivity is created in the target, the velocity-sensitive gradient pulses may be turned off or gradient pulses with zero first moment may be used. In some examples, the velocity-selective pulse may include a Fourier-transform based velocity-selective pulse train with a predefined amplitude modulation. For example, each pulse may be a composite RF pulse. In some embodiments, the velocity-selective pulses may be velocity-selective inversion pulses. One example of the composite RF pulses includes refocusing pulses. In some embodiments, the refocusing pulses may include a phase cycling pattern such as the Malcom-Levitt phase cycling patterns. In the applied pulses, the composite pulses may include gaps before or after the gradient pulses.

As disclosed herein through discussion and results, the RF signal may be applied such that a resulting signal-to-noise ratio efficiency of the acquired magnetic resonance signal is higher than that of an existing non-velocity-selective labeling method (e.g., methods discussed in FIG. 5 of the present document) at a temporal resolution of 1.5 seconds. For example, the existing method may be a method that applies pulsed or pseudo-continuous labeling. For example, the amplitude, phase a number of times applied, or timing of the RF signal may be controlled to ensure SNR efficiency above existing methods.

In some embodiments, the method 600 may be used to perform MRI imaging of a target that includes multiple slabs of a biological material. The predetermined threshold of signal quality may be maintained for MRI signal acquired from each of the multiple slabs. In some embodiments, this may be achieved by acquiring the MRI images in a 2D or a 3D (three dimensional) mode.

Figure 7:
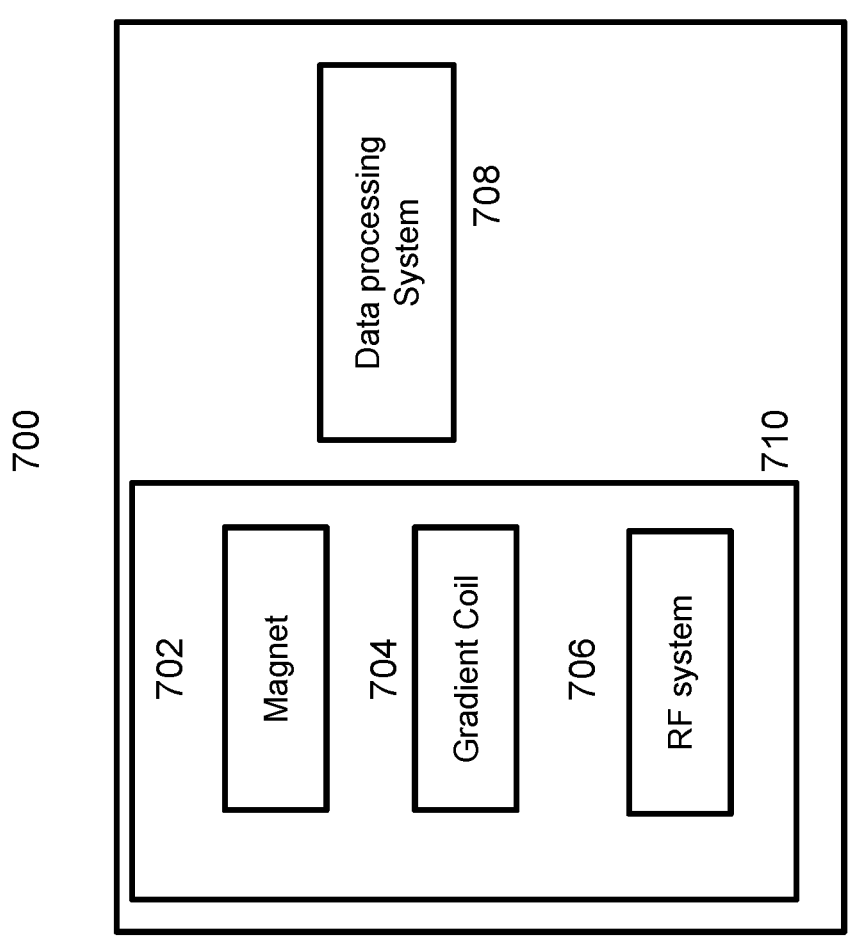
FIG. 7 is a block diagram of an example MRI system.

FIG. 7 is a block diagram of an example of an MRI system 700. The system includes a scanner (710) comprising one or more magnets (702), one or more gradient coils (704) and a radio frequency (RF) system (706). The MRI system 700 further includes a data processing system 708 in communication with the scanner 710 to receive the acquired magnetic resonance signals and generate an MRI image of the target from the magnetic resonance signal. The scanner 702 may be configured to scan a target during the process of acquiring an MRI image. The gradient coils 704 may be used to apply electromagnetic signals to the target using the magnets. The RF system 706 may be configured to generate the composite pulse as described in the present document. A processor (not explicitly shown) may control operation of the scanner 710 and the data processing system 708. In some embodiments, the data processing system 708 may include a processor, a memory and optionally hardware circuitry to implement image processing algorithms for generation of an MRI image.

In some embodiments, the processor may be configured to control operation of the above-described MRI system. The processor may control the gradient coils RF systems to generate a composite pulse as described in the present document and control the scanner to capture electromagnetic response generated by the target. The processor may process the data collected from the scanner and generate an MRI image of the target.

4. Further Discussion

The nb-VS labeling may be designed within ±40 cm/s, likely sufficient for brain imaging. Because FT-VSI has a periodic inversion pattern, to avoid potential perturbation of spins at higher velocities, slice selectivity may be applied.

In general, the inversion bandwidth may affect the BD, and subsequently the temporal resolution and SNR efficiency. Adjusting the bandwidth would also change the period of the inversion bands. In practice, these parameters may be adjusted based on RF and MRI characteristics of the target whose image is desired to be acquired.

The temporal resolution and SNR efficiency of PASL (pulse arterial spin labeling) can be significantly improved by Turbo-ASL, though the quantification is not straightforward. For nb-VS labeling, the image acquisition requires a matched VS profile for quantification. Conventional slice-selective excitation with vascular crushing may interfere with the spins moving at high velocities. Therefore, in some embodiments, an excitation tailored for VS labeling may be used for nb-VSASL.

5. Further Details of VSASL

In the VSASL technique, spins are globally labeled on the basis of flow velocity, eliminating the gap, as well as the associated heterogenous TDs (Transit Delays) in conventional ASL. Eliminating the heterogenous TDs in the ASL guarantees that a single optimal post-labeling delay (PLD) is always available to measure perfusion with both accuracy and maximized signal to noise ratio (SNR) efficiency. VSASL acquires images under two preparation conditions: label and control. Using VSASL with VSS labeling as an example, under the label condition, the arterial blood is labeled by VSS modules consisted of radio frequency (RF) pulses and flow-weighting gradients, and the spins moving above a chosen cutoff velocity (Vc) are saturated. Under the control condition, the VSS modules are applied without the flow weighting gradients, leaving the spins unperturbed. The difference between the two conditions is a bolus of labeled spins that is moving above the Vc at the time of labeling. After a delay, perfusion-weighted images are acquired with flow-weighting gradients of the same Vc, generating a VSASL signal that consists of blood that has decelerated through Vc. Note that it is essential to match the Vc in the image acquisition.

6. A Comparison of Various VSASL Schemes

Velocity-selective pulses fit into 2 categories: VS saturation pulses (VSS) and VS Inversion (VSI) pulses. VSS pulses tip the magnetization into the transverse plane briefly before tipping it back to the longitudinal axis. A combination of RF and gradient pulses can be used to dephase the magnetization of spins traveling above a given cutoff velocity (Vc) during the process. These fast-moving spins are effectively saturated through the mixing effect given a laminar flow distribution. The last segment in a VSS pulse tips the magnetization back to the longitudinal axis. Under the control condition, all the spins are tipped down to the transverse plane and then back to the longitudinal axis without dephasing: thus, the magnetization remains unperturbed except for the same relaxation effects as under the label condition. Fourier transform-based VSI pulses consist of velocity encoding RF and gradient pulses that will only invert the spins traveling at the selected velocity (typically near 0). Under the control condition in VSI, all spins are inverted.

Their SNR efficiency and robustness against B1, B0, and EC effects were evaluated through Bloch simulation, phantom, and human experiments. Both dual-sBIR8-VSS and sinc-VSI measured the highest SNR efficiency in vivo among the VS labeling schemes investigated. Overall, the dual-sBIR8-VSS pulse was the most robust VS labeling strategy against field imperfections. Whereas the sinc-modulated VSI pulse showed greater tSNR and was the best among the VSI methods, further technical improvement.

7. Bloch Simulations

The overall ASL signal was calculated by summing up the ASL signal at different mean velocities with such weights to account for the effective population available for labeling and its SNR efficiency is calculated accordingly.

The SNR efficiency is defined as SASL divided by square root of 2TR, that is, $Sig_{ASL}/\sqrt{2TR}$, where $S_{ASL}$ is the ASL signal measured in two time to repetitions (TRs) (a pair of label/control acquisitions). For comparison, the SNR efficiencies of pulsed ASL (PASL) and pseudocontinuous ASL (PCASL) were also simulated. For all the labeling methods, the maximal SNR efficiency was calculated at each TR (from 1 to 8 s, with a step size of 0.05 s), and then normalized to that of the VSASL-1VSS at TR of 1 s. A T1 of 1.66 s and a T2 of 0.15 s were assumed for arterial blood. An imaging time of 0.3 s was assumed.

In one example implementation, the segmented-sinc-VSI pulse may be constructed by subdividing a 180°, single-lobed sinc pulse into 9 pieces of equal duration. In contrast, the sinc-VSI pulse was constructed by concatenating 9 rectangular pulses with a single-lobed sinc modulation (the amplitude of the nth pulse is given by sinc $(n\pi/5-\pi)$, where n=1, 2, . . . , 9). The flip angles of these 9 rectangular pulses add up to 180°.

8. Conclusion

It will be appreciated by one of skill in the art that the present document discloses an nb-VS labeling for ultra-fast perfusion fMRI with high SNR efficiency. In one advantageous aspect, the disclosed techniques may be used by embodiments to improve the temporal resolution and/or SNR efficiency of perfusion imaging using velocity-selective (VS) labeling, by purposely labeling spins within a narrow velocity band. This strategy allows faster recovery/refreshment of the magnetization of arterial spins for improved SNR efficiency and temporal resolution. A few implementation methods of such labeling strategy have been disclosed, using modified Fourier-transform based VS inversion pulses. The SNR efficiency and achievable temporal resolution were examined by ASL signal modeling, demonstrating a good promise for ultra-fast perfusion imaging with high SNR efficiency.

While this specification contains many specifics, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The described systems, apparatus and techniques can be implemented in electronic circuitry, computer hardware, firmware, software, or in combinations of them, such as the structural means disclosed in this specification and structural equivalents thereof. This can include at least one computer-readable storage medium embodying a program operable to cause one or more data processing apparatus (e.g., a signal processing device including a programmable processor) to perform operations described. Thus, program implementations can be realized from a disclosed method, system, or apparatus, and apparatus implementations can be realized from a disclosed system, computer-readable medium, or method. Similarly, method implementations can be realized from a disclosed system, computer-readable medium, or apparatus, and system implementations can be realized from a disclosed method, computer-readable medium, or apparatus.

Only a few implementations are disclosed. However, variations and enhancements of the disclosed implementations and other implementations can be made based on what is described and illustrated in this specification.

The invention claimed is:

1. A method of operating a magnetic resonance imaging (MRI) system, comprising:

applying a radio frequency (RF) signal of a predetermined time duration towards a target, wherein the RF signal comprises a composite pulse that includes a velocity-selective pulse comprising RF pulses whose phase shift is modulated over the predetermined time duration;

acquiring a magnetic resonance signal from the target resulting from the application of the RF signal; and generating an MRI image of the target from the magnetic resonance signal;

wherein the applying is performed by controlling spins generated in the target such that spins moving within a predetermined velocity band are magnetization-modulated while static and spins moving at velocities outside of the predetermined velocity band remain unaffected;

wherein the predetermined velocity band is from 0.5 cm/s to 20 cm/s.

2. The method of claim 1, wherein the phase shift is modulated using a predetermined function.

3. The method of claim 2, wherein the predetermined function is a linear function.

4. The method of claim 1, wherein the RF signal is applied without creating velocity-selectivity in the target.

5. The method of claim 1, wherein the velocity-selective pulse comprises a Fourier-transform based velocity-selective pulse train with a predetermined amplitude modulation.

6. The method of claim 5, wherein the Fourier-transform based velocity-selective pulse train includes composite RF pulses.

7. The method of claim 1, wherein the composite pulse includes refocusing pulses or gaps before and after gradient pulses.

8. A method of operating a magnetic resonance imaging (MRI) system, comprising:

applying a radio frequency (RF) signal of a predetermined time duration towards a target, wherein the RF signal comprises a composite pulse that includes a velocity-selective pulse comprising RF pulses whose phase shift is modulated over the predetermined time duration;

acquiring a magnetic resonance signal from the target resulting from the application of the RF signal; and generating an MRI image of the target from the magnetic resonance signal, wherein the applying the RF signal comprises controlling the RF signal such that a resulting signal-to-noise ratio efficiency of the acquired magnetic resonance signal is higher than that of an existing non-velocity-selective labeling method at a temporal resolution of 1.5 seconds.

9. The method of claim 8, wherein the phase shift is modulated using a predetermined function.

10. The method of claim 9, wherein the predetermined function is a linear function.

11. The method of claim 8, wherein the RF signal is applied without creating velocity-selectivity in the target.

12. The method of claim 8, wherein the velocity-selective pulse comprises a Fourier-transform based velocity-selective pulse train with a predetermined amplitude modulation, wherein the Fourier-transform based velocity-selective pulse train includes composite RF pulses.

13. A magnetic resonance imaging (MRI) apparatus, comprising:

a scanner comprising a magnet, gradient coils and a radio frequency (RF) system to perform operations comprising:

applying a radio frequency (RF) signal of a predetermined time duration towards a target, wherein the RF signal comprises a composite pulse that includes a velocity-selective pulse comprising RF pulses whose phase shift is modulated over the predetermined time duration;

acquiring a magnetic resonance signal from the target resulting from the application of the RF signal; and a data processing system in communication with the scanner to receive the acquired magnetic resonance signals and generate an MRI image of the target from the magnetic resonance signal;

wherein (a) the applying is performed by controlling spins generated in the target such that spins moving within a predetermined velocity band are magnetization-modulated while static and spins moving at velocities outside of the predetermined velocity band remain unaffected and the predetermined velocity band is from 0.5 cm/s to 20 cm/s; or (b) the applying the RF signal comprises controlling the RF signal such that a resulting signal-to-noise ratio efficiency of the acquired magnetic resonance signal is higher than that of an existing non-velocity-selective labeling method at a temporal resolution of 1.5 seconds.

14. The apparatus of claim 13, wherein the RF signal is applied by controlling spins generated in the target such that spins moving within a predetermined velocity band are magnetization-modulated while static and spins moving at velocities outside of the predetermined velocity band remain unaffected.

15. The apparatus of claim 13, wherein the phase shift is modulated using a linear function.

16. The apparatus of claim 13, wherein the RF signal is applied without creating velocity selectivity in the target.

17. The apparatus of claim 13, wherein the velocity-selective pulse comprises a Fourier-transform based velocity-selective pulse train with a predetermined amplitude modulation.

18. The apparatus of claim 17, wherein the Fourier-transform based velocity-selective pulse train includes composite RF pulses.

19. The apparatus of claim 13, wherein the target comprises multiple slabs of a biological material and wherein a predetermined threshold of signal quality is maintained in the acquired magnetic resonance signal for all of the multiple slabs.

20. The apparatus of claim 13, wherein the composite pulse includes refocusing pulses or gaps before and after gradient pulses.

* * * * *